United States Patent [19]

Cocks et al.

[11] Patent Number: 4,821,301

[45] Date of Patent: Apr. 11, 1989

[54] X-RAY REFLECTION METHOD AND APPARATUS FOR CHEMICAL ANALYSIS OF THIN SURFACE LAYERS

[75] Inventors: Franklin H. Cocks; Roland Gettliffe, both of Durham, N.C.

[73] Assignee: Duke University, Durham, N.C.

[21] Appl. No.: 834,919

[22] Filed: Feb. 28, 1986

[51] Int. Cl.[4] ............................................. G01N 23/20
[52] U.S. Cl. ......................................... 378/70; 378/85
[58] Field of Search ................... 378/1, 70, 85, 45, 53, 378/83, 88, 210, 84

[56] References Cited

U.S. PATENT DOCUMENTS

| | | |
|---|---|---|
| 3,011,060 | 11/1961 | Dorenbosch et al. |
| 3,370,167 | 2/1968 | Sterk. |
| 3,409,769 | 11/1968 | McKinney et al. |
| 3,418,466 | 12/1968 | Herglotz ............................. 378/70 |
| 3,702,933 | 11/1972 | Fields et al. ........................ 378/70 |
| 3,925,678 | 12/1975 | Eberspaecher et al. |
| 4,169,228 | 9/1979 | Briska et al. ....................... 378/45 |
| 4,382,181 | 5/1983 | Wang. |
| 4,567,605 | 1/1986 | Bartels ................................ 378/85 |

OTHER PUBLICATIONS

Mozzi et al., "Adaptation of an X-Ray Diffractometer for Thin Film Studies by Total Reflection of X-Rays", Rev. of Scientific Instruments, vol. 35, No. 1, Jan. 1964, pp. 75-78.

"Voltrage Von Der Tagung Des Gauvereins Sachsen--Thuringen-Schlesien Der Deutschen . . . " by Sangewald u. WeiBberger, Physik. Zeitschr. XXX Jan. 20, 1929, pp. 268-273.

"Reflectometry (Review)" by Sinaiskii and Sidenko, Instruction and Experimental Techniques, vol. 17, No. 6, Nov.-Dec. 1974, pp. 1551-1557.

"Application of Energy Dispersive X-Ray Fluorescence for the Determination of Selenium in Blood and Tissue" by Hotynska and Markowicz, Radiochem. Radioanal. Letters, 31(3), Nov. 1, 1977, pp. 165-170.

"Comparison of Thin Film Analytical Methods" by Werner, Proc. 7th Intern. Vac. Congr. & 3rd Intern. Conf. Solid Surfaces (Vienna 1977).

"Characterization of Thin Layers on Perfect Crystals With a Multipurpose High Resolution X-Ray Diffractometer" by Bartels, J. Vacuum Science Technology B, vol. 1, No. 2, Apr.-Jun. 1983, pp. 338-345.

"Electroanalytical Study of Tricyclic Anitdepressants" by Biship and Hussein, Analyst, vol. 109, Jan. 1984, pp. 73-80.

Primary Examiner—Craig E. Church
Assistant Examiner—T. N. Grigsby
Attorney, Agent, or Firm—Richard E. Jenkins

[57] ABSTRACT

X-rays can be physically reflected from surfaces under certain conditions and quantitative measurements of the reflected X-ray intensity around the critical angle for X-ray reflection may be utilized to provide a method for the chemical analysis of very thin surface layers or thin films including adsorbed organic films. This method of chemical analysis is based on different physical principles than the well-known X-ray diffraction or fluorescence methods. The X-ray reflection method for the chemical analysis of thin surface layers depends on the influence of the X-ray absorptivity of the surface layers upon the concomitant angular or wavelength dependence of the intensity of the reflected X-ray. Because the reflected wave does not significantly penetrate the sample, the sample depth for chemical analysis by the reflected X-ray beam can be very thin, for example about 100 angstroms in thickness.

9 Claims, 8 Drawing Sheets

```
                                    ┌─────────┐
                                    │  Start  │
                                    └────┬────┘
    ┌──────────────────────────────────────────────────────────────────┐
    │ Subject surface composed of known elements in known proportions, │
    │ including sulfur, to X-ray radiation of substantially monochromatic │
    │           wavelength λ at a glancing angle Θ                      │
    └──────────────────────────────┬───────────────────────────────────┘
                          ┌────────┴──────────────┐
                          │ Vary the glancing angle Θ │
                          └────────┬──────────────┘
              ┌────────────────────┴─────────────────────┐
              │ Measure the reflected X-ray intensities relative │
              │  to the intensity of the incident X-ray beam as a │
              │         function of glancing angle Θ              │
              └────────────────────┬─────────────────────┘
```

- Compute integrated area under measured curve from where $I/I_0$ equals 0.5 ($\Theta_{0.5}$) to where $I/I_0$ equals zero
- Assume sulfur content of surface
- Compute $\delta$
- Compute $\mu$
- Compute $\beta$
- Compute $K$
- Compute $\Theta_c$
- Compute $q$
- Compute $a^2/2$
- Compute $a$
- Compute $I/I_0$
- Compute the integrated area under calculated curve
- Compute integrated area as a function of different sulfur contents
- Compare calculated and measured integrated area
- Print sulfur content
- End

X-RAY REFLECTION METHOD AND APPARATUS FOR CHEMICAL ANALYSIS OF THIN SURFACE LAYERS

TECHNICAL FIELD

This invention relates to the use of X-ray reflection to chemically analyze thin layers of certain materials deposited on a suitable substrate. Measurement of X-ray intensity is made around the critical angle for X-ray reflection and as a function of incident X-ray wavelength at a fixed reflection angle to chemically analyze the substance of interest.

BACKGROUND ART

It is well known that X-rays can be diffracted from crystalline solids to produce diffraction patterns whose interpretation gives information on the atomic structure of such crystalline materials. It is also well known that X-rays can be used to excite fluorescent emissions from materials, and that the fluorescent emissions can be used to provide information on the composition of the materials exposed to the incident X-rays. Additionally, it is well known that X-rays can be reflected from smooth surfaces if the reflection angle between the incident X-rays and the surface is less than some critical value. Indeed, the use of the reflection of X-rays from smooth surfaces is a basic feature of the design of X-ray telescopes. Because the image forming quality of such telescopes depends in part on the smoothness of the reflecting surface, studies have been made of the influence of surface topography on the reflected X-ray beam.

The apparatus and method of the present invention relate to the use of X-ray reflection to determine the chemical composition of the surface from which the X-rays are reflected. Because the X-ray beam is being reflected and not diffracted, it is not required that the reflecting surface be crystalline in nature and the chemical composition of either crystalline or amorphous surfaces can be equally well determined. By the choice of particular incident X-ray wavelengths it is possible to analyze the composition of surfaces composed of any of the known elements, including elements of low atomic number. When X-ray fluorescent methods, such as that taught by Dorenbosch and Zingaro in U.S. Pat. No. 3,011,060 are used for such analyses, there will be elements of low atomic number, such as carbon (atomic number 6) and nitrogen (atomic number 7) which cannot be easily detected because the fluorescent X-rays from such atoms are very weak and are of very long wavelength. The X-ray wavelength characteristic of fluorescent sulfur, atomic number 16, is already approximately 5.4 angstroms while the X-ray wavelength characteristic of carbon, atomic number 6, is more than 44 angstroms. The fluorescent wavelength characteristic of lithium, atomic number 3, is 228 angstroms. The present invention is not so limited because it does not depend upon the excitation of the fluorescent radiation. Additionally, the present method is capable of analyzing much thinner layers than are other X-ray methods and layers of only 100 angstroms can be analyzed due to the fact that the X-rays are being reflected and so do not penetrate as significantly into the surface being analyzed as do normal X-ray analytical procedures.

DISCLOSURE OF THE INVENTION

The present invention relates to a nondestructive method for the chemical analysis of surfaces, including thin surface layers. In one example of the present invention, the surface to be analyzed is exposed to substantially monochromatic X-rays at a low angle of incidence, the X-rays being totally reflected due to the fact that the surface's index of refraction for X-rays is less than unity. The reflected X-rays can be detected by instrumentation designed to record the reflected intensity as a function of glancing angle as this angle is swept from values below the critical angle to values above the critical angle, thereby creating a record of the reflection characteristics of the surface being examined in the form of reflected intensity as a function of glancing angle curves.

It is therefore an object of the present invention to provide a method for the nondestructive chemical analysis of surfaces, including thin surface layers.

It is another object of this invention to provide a method for the analysis of adsorbed organic films which are amorphous and not crystalline and which furthermore are composed substantially of elements of low atomic number.

It is still another object of this invention to provide a method for the analysis of organic material which does not require that the organic material to be analyzed be exposed to a vacuum.

It is yet another object of this invention to provide a method for the quantitative analysis of surfaces for particular elements by observing the change in intensity at a fixed reflection angle of the reflected intensity as the wavelength of the incident X-rays is increased through a range of values.

These and other objects and features of the present invention will become more fully apparent from the following description and appended claims taken in conjunction with the accompanying drawings.

BEST MODE FOR CARRYING OUT THE INVENTION

Reference should be made to FIGS. 1-4 as necessary to appreciate the description set forth hereinafter. The reflection of X-rays from surfaces occurs because the index of refraction of X-rays for solids is less than unity. Thus, by Snell's law, at some glancing angle, $\theta$, the transmitted X-ray intensity will fall to zero. For an X-ray traveling from medium 1 (typically air or vacuum) for which the index of refraction is $\eta 1$ to medium 2 for which the index of refraction is $\eta 2$, the critical glancing angle, $\theta c$, is given by $$\cos(\theta c) = \eta 2/\eta 1 \quad \text{(Equation 1)}$$

For glancing angles less than $\theta c$, the X-ray will be totally reflected by medium 2 back into medium 1. In the case of X-rays, the index of refraction of air is, within one part in more than ten billion, equal to unity. For solid substances, the index of refraction for X-rays is slightly less than unity and can be written as $$\eta = 1 - \delta \quad \text{(Equation 2)}$$

The critical angle $\theta c$ at which total reflection of the X-rays occurs is thus given by $$\theta c = (2\delta)^{\frac{1}{2}} \quad \text{(Equation 3)}$$

where $\delta$ is the amount by which the index of refraction of the X-rays is less than unity. If the reflecting surface does not absorb the incident X-rays, then all of the intensity of the incident X-rays will go into the reflected X-ray beam. It is usually the case, however, that some absorption of the X-rays will occur, in which case the index of refraction, $\eta$, of the X-rays will be written as a complex number of the form $$\eta = 1 - \delta - i\beta \quad \text{(Equation 4)}$$

in which i indicates that the term in which it is written must be treated as an imaginary quantity and $\beta$ is a term which depends on the linear absorption coefficient of the reflecting surface for the incident X-rays. The variables of interest in this method are therefor the reflected intensity, I, the incident intensity, $I_o$, the glancing angle, $\theta$, the value $\delta$ by which the index of refraction of the material is less than unity for incident X-rays of wavelength $\lambda$, and $\beta$ the absolute magnitude of the imaginary portion of the index of refraction of the material for incident X-rays of wavelength $\lambda$. These variables may be combined such that the ratio of I to $I_o$ is some functional combination of $\theta$, $\lambda$, $\delta$, and $\beta$ such that $$I/I_o = f(\theta, \lambda, \delta, \beta) \quad \text{(Equation 5)}$$

where $f(\theta, \lambda, \delta, \beta)$ indicates that $\theta$, $\lambda$, $\delta$, and $\beta$, in some functional form, can be arranged to give the value of $I/I_o$.

As shown by Jentzch in *Physikalische Zeitschrift*, Volume 30, 1929, one functional form of the ratio of reflected intensity I, to the incident intensity $I_o$ can be given by $$\frac{I}{I_0} = \frac{1 - aq + a^2/2}{1 + aq + a^2/2} \quad \text{(Equation 6)}$$

where
$a^2/2 = q^2 - 1 + [(q^21)^2 + K^2]^{\frac{1}{2}}$
$q = \theta/\theta c$
$K = \mu\lambda/4\pi\delta = \beta/\delta$
$\theta c = (2\delta)^{\frac{1}{2}}$ where $\mu$ is the linear absorption coefficient of the material for the incident X-rays, $\theta c$ is the critical angle for total reflection, and $\theta$ is the angle at which the reflected beam intensity I is measured.

Of particular importance for the present invention is the linear absorption coefficient, $\mu$. For a surface that contains N different elements, the overall linear absorption coefficient, $\mu$, for the surface can be calculated from $$\mu = \sum_n \left(\frac{\mu_n}{\rho_0}\right)_n \rho_n \quad \text{(Equation 7)}$$

where $\rho n$ is the amount, usually written as grams per cubic centimeter, of element n in the surface. The values $$\left(\frac{\mu_n}{\rho_0}\right)_n$$

are found in tables of mass absorption coefficients of each element n for the X-ray wavelength being used. Such a Table is found, for example, in Volume III of the *International Tables for X-Ray Crystallography*, published by Kynock Press, Birmingham, England and in *Advances in X-Ray Analysis*, Volume 17, published by Plenum Press, New York, pp. 150-213. In these expressions, $\rho_o$ is the density of the pure element n.

From dispersion theory, as illustrated in Sinaiskii and Sidenko in *Instrumentation and Experimental Technique*, Volume 17, Number 6, 1974, values of $\delta$ can be calculated from $$\delta = \frac{e^2\lambda^2 N_{Avo}}{2\pi mc^2} \sum_n \frac{\rho_n}{A_n}\left(Z_n + Z_{kn}\frac{\lambda^2}{\lambda_{kn}^2}\ln\left[1 - \frac{\lambda^2}{\lambda_{kn}^2}\right]\right) \quad \text{(Equation 8)}$$

where $N_{Avo}$ is Avogadro's number, $A_n$ is molecular weight, $Z_n$ is the atomic number, $\lambda_{kn}$ is the absorption edge, and $Z_{kn}$ is the number of electrons in the k level for element n. Also, $\lambda$ is the wavelength of the incident radiation, c is the speed of light, e is the charge of an electron, and m is the mass of an electron.

By means of these equations the expected dependence of the reflected X-ray intensity I can be calculated for any assumed surface chemical composition. What is desired, however, is to know the surface chemical composition from the measured reflected X-ray intensity I as a function of the reflection angle $\theta$. Such a calculation can be made by comparing the measured ratio of the reflected intensity I and the incident intensity $I_o$ as a function of reflection angle $\theta$ to the calculated ratio of reflected to incident intensities computed according to equations given above, and to repeat this computation with different assumed surface compositions until the measured curve is duplicated by the calculated curve. If, however, two different assumed surface compositions give the same value of $\mu$, then it will be found that the calculated $I/I_o$ versus $\theta$ relationship is not sensitive to changes in surface composition since only the variation in $\delta$ with varying surface composition will affect the $I/I_o$ versus $\theta$ relationship.

In such a case it will be beneficial to expose the surface that is to be analyzed to a sequence of more than one incident X-ray wavelength and to choose the wavelengths such that $\mu$ does vary with composition for at least one of the chosen wavelengths and measure the resulting $I/I_o$ versus $\theta$ relationships. If the wavelengths used are chosen so that the calculated linear absorption coefficients $\mu$ is strongly dependent upon assumed surface composition, then the accuracy of the resultant calculated surface composition will be improved.

For example, if a film is to be examined for sulfur content, then it will be recognized that the use of an X-ray wavelength which is near but less than the wavelength of the L-level absorption edge for sulfur will be advantageous. The L-level absorption edge for sulfur occurs near 80 angstroms. Thus, if the incident wavelength chosen is M-zeta characteristic radiation of niobium which has a wavelength of 72.2 angstroms, the effect of sulfur will be accentuated. Specifically, for the 72.2 angstrom X-rays, the mass absorption coefficient $$\frac{\mu_n}{\rho_0}$$

for sulfur is 79,780 cm²/gram.

It will be understood that the incident X-ray beam should be substantially monochromatic or be composed of a known function of intensities at different wavelengths. Substantially monochromatic X-ray beams can be produced by any of a variety of methods including X-ray fluorescence of different materials, use of X-ray filtering methods, X-ray lasers, X-ray diffraction gratings, two-crystal monochromators, or four-crystal monochromators of Bartels' design. This latter monochromator is particularly favorable since it is easily tunable and can be used to produce monochromatic X-ray beams over a range of wavelengths. As shown by Bartels in the April-June issue of the *Journal of Vacuum Science and Technology*, 1983, and in U.S. Pat. No. 4,567,605, a monochromator utilizing successive X-ray diffraction from four successive crystals can produce substantially monochromatic X-ray beams of any desired wavelength over a range of wavelengths. For traditional X-ray investigations which involve the characteristc X-ray radiation for high atomic number elements such as copper, atomic number 29, for which the K-alpha characteristic radiation is approximately 1.54 angstroms in wavelength, Bartels' monochromators will preferably be constructed utilizing crystals such as germanium for which the interatomic plane spacings are approximately 1 angstrom. For use in the long wavelength region of the present invention, the crystals used in the monochromator of Bartels' design should have interatomic plane spacings in the range of the wavelength of the X-rays used, preferably in the range from 5.4 to 228 angstroms. Since normal crystalline materials do not commonly possess interatomic plane spacings of more than a few angstroms, it will be necessary to use synthetic layered microstructures to produce the required large X-ray diffraction spacing needed for the desired long wavelengths.

Four examples of applications of the present invention will now be given. It will be appreciated that these examples do not represent an exhaustive listing of the range of applications.

EXAMPLE 1

Analysis of the Surface Composition of a Film of Se and Te

The elements selenium (Se) and tellurium (Te) are soluble in all proportions and amorphous thin films of Se-Te can be prepared by the evaporation of Se and Te from a master alloy composed of 50-50 atom percent of Se and Te onto an optically flat substrate. The brief exposure to this substrate using a mechanical shutter produces a thin ($\cong 1$ micron thick) amorphous Se-Te film. As shown by Cocks and Gettliffe in *Materials Letters*, Volume 3, March, 1985, this film can be used to reflect the X-rays produced by a copper anode X-ray tube operated at 18.5 kV and 1 milliampere after these X-rays have been rendered substantially monochromatic with a wavelength of 1.54 angstroms by passage through a 0.1 mm thick nickel filter. The intensity of the reflected X-rays can then be measured as a function of the reflecting angle, $\theta$, by means of a goniometer stage fitted with micrometers for precise sample positioning with respect to the incident beam. The critical angle for total reflection will be found to occur at an angle of $\theta c$ of approximately 0.29 degrees, at which point the intensity of the reflected X-ray beam will be found to decrease strongly with increasing angle $\theta$ in accordance with the equations previously given. By means of these equations, knowing that substantially only Se and Te comprise the film, the maximum rate of decrease in the reflected intensity with increasing angle can be calculated as a function of assumed film composition. This maximum value for the rate of change in reflected intensity ratio $I/I_o$ with respect to reflection angle $\theta$ will be found to vary from more than 20/degree to 8/degree as the assumed film composition varies from pure Se to pure Te. For the measured film the maximum value was found to be 14.01/degree, corresponding to a surface film composition of 38 atom percent Te by the use of the equations previously given.

EXAMPLE 2

Analysis of the Adsorbed Films of Tricyclic Compounds on Platinum Substrates

Figure 1:
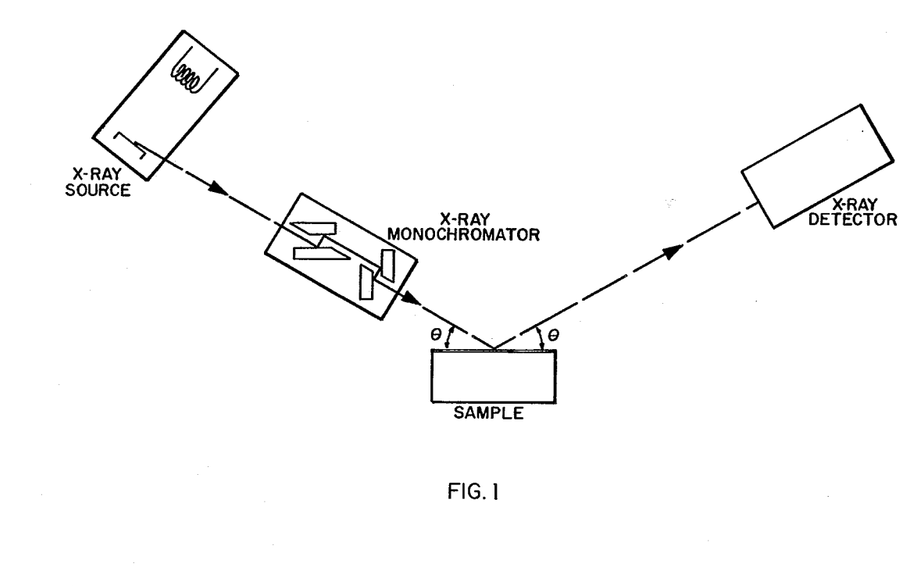
FIG. 1 is a schematic representation of the apparatus of the invention utilizing a monochromator of Bartels' design.
Figure 2:
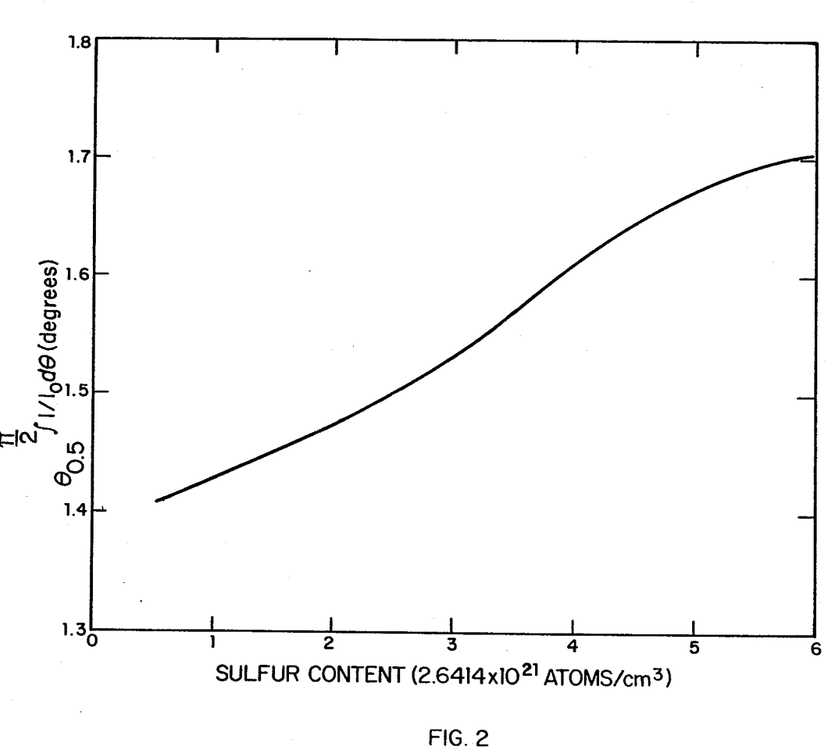
FIG. 2 depicts the calculated relationship between the integrated area under the curve of $I/I_o$ versus $\theta$ from where $I/I_o$ equals 0.5 ($\theta = \theta_{0.5}$) to where $I/I_o$ is essentially 0 for X-ray reflection curves for tricyclic antidepressant adsorbed films on platinum as a function of sulfur content.
Figure 5:
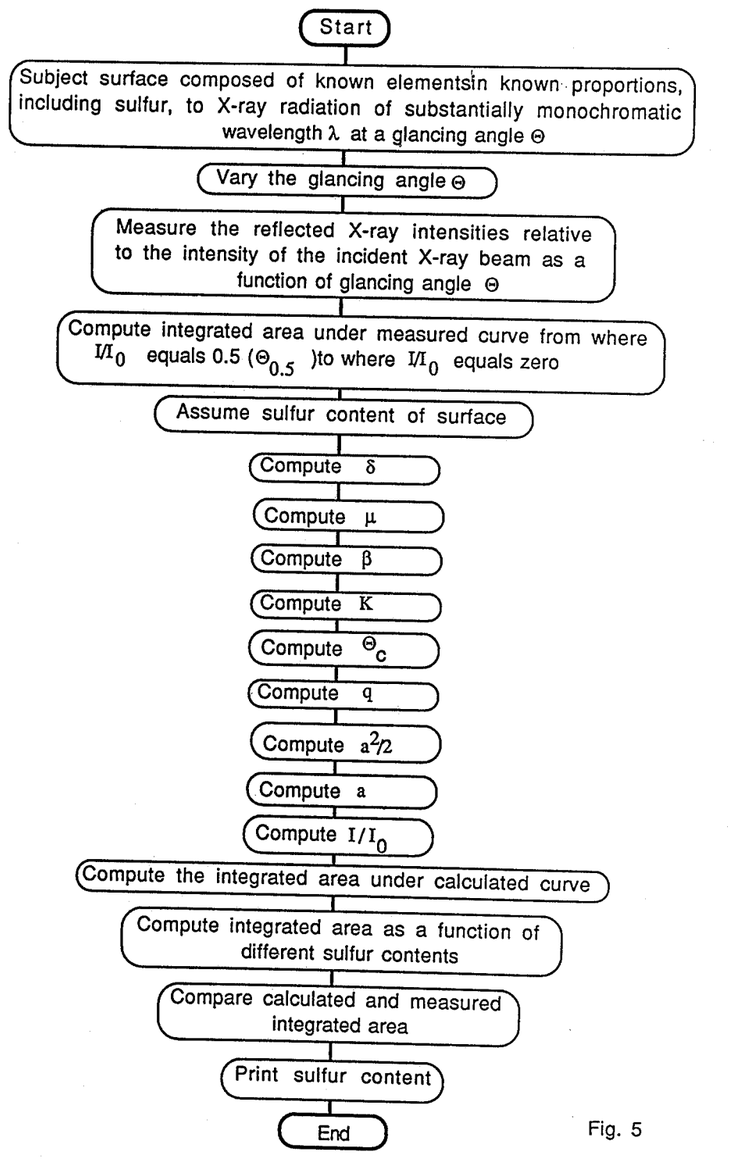
FIG. 5 depicts the sequence of steps involved in calculating the quantity of a single element in a surface by means of the integrated area under the measured $I/I_0$ versus $\theta$, over the given $\theta$ range $\theta_{0.5}$ to where $I/I_0$ is zero, compared to the calculated area.
Figure 6:
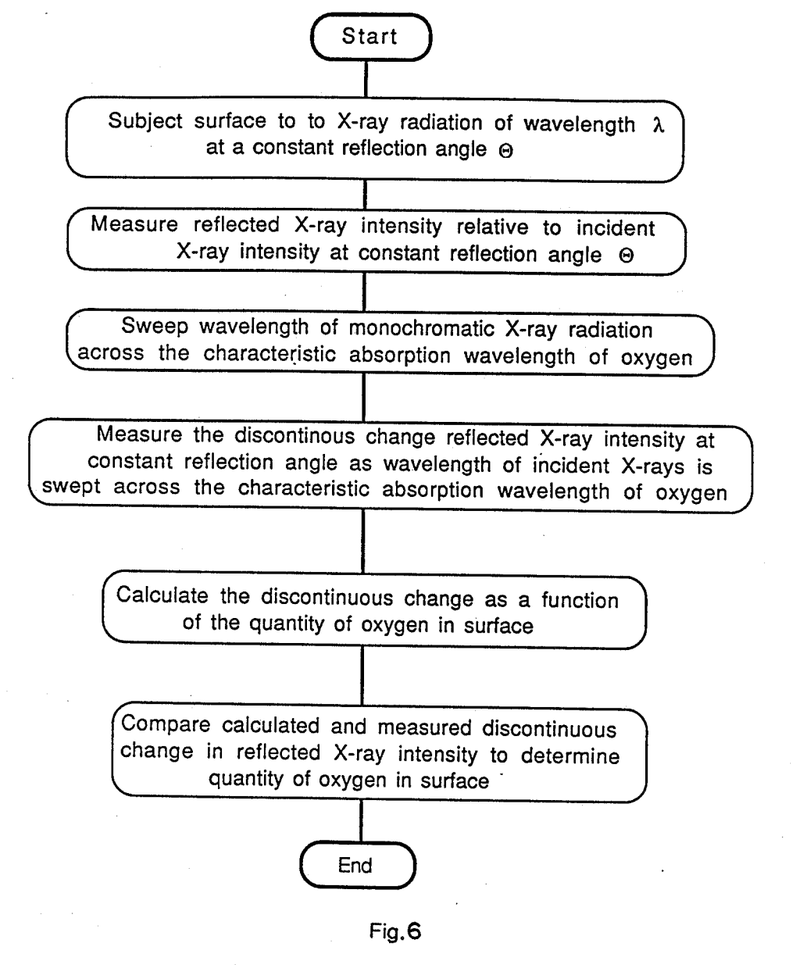
FIG. 6 depicts the sequence involved in calculating the quantity of a single element in a surface from the magnitude of the discontinuous change in the measured curve of reflected X-ray intensities as the incident X-ray wavelength is swept across the characteristic absorption wavelength of the elements.
Figure 7:
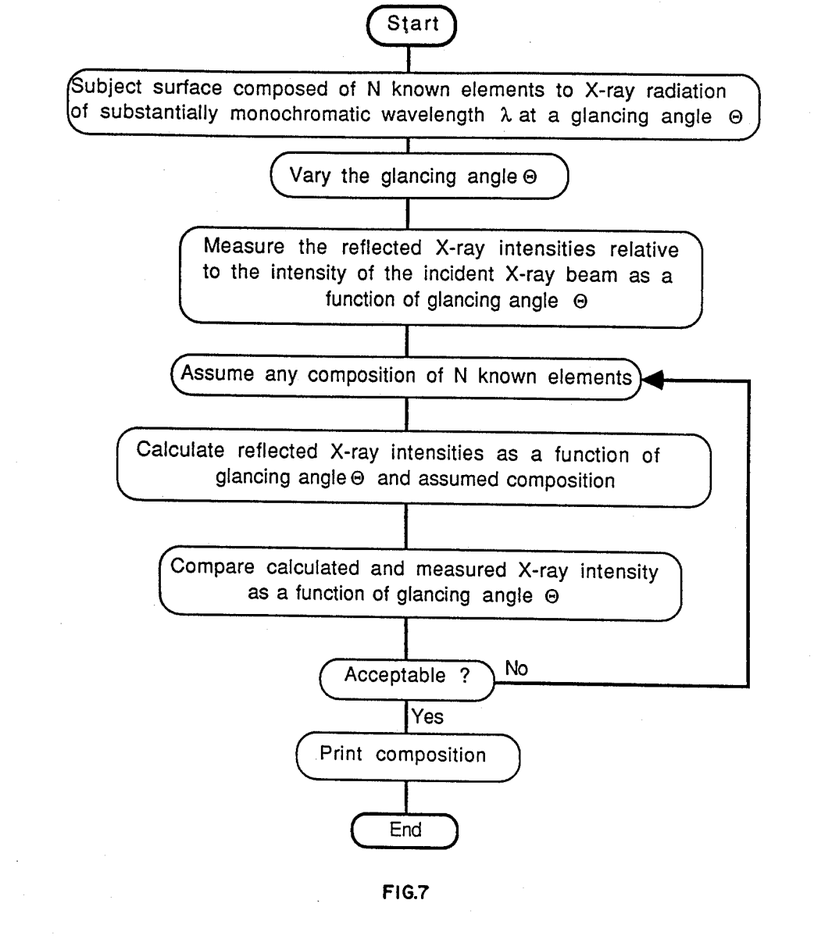
FIG. 7 depicts a flow chart illustrating the sequence of steps involved in calculating surface composition from the measured reflected X-ray intensities in the most general case.
Figure 8:
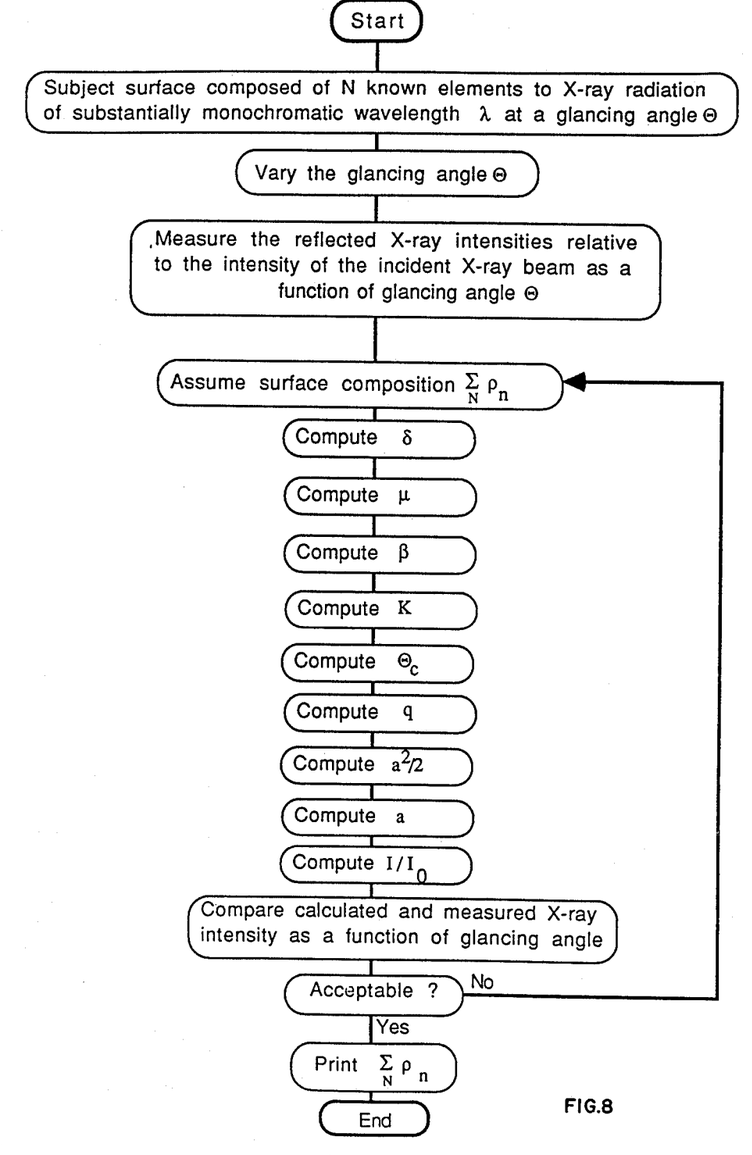
FIG. 8 is a graph illustrating the sequence of steps involved in calculating the surface composition from the measured reflected X-ray intensities in the case of the use of Equations 4 through 8.

As shown by Bishop and Hussein in the January, 1984 issue of *The Analyst*, Volume 109, tricyclic antidepressant compounds will adsorb onto platinum and platinum films. These compounds have similar chemical structures and in some cases differ only in their precise composition. Amytriptyline, for example, has the formula $C_{20}H_{21}ClN$ while dothiepin has the formula $C_{19}H_{20}ClNS$. Both materials have the same tricyclic benzene ring structure with HCl and $C_5H_{12}N$ side groups. By using niobium M-zeta X-rays at 72.2 angstroms wavelengths, a reflection pattern may be obtained which is strongly dependent on sulfur content of the films that will be adsorbed onto platinum films deposited onto optically flat glass slides when such platinum coated glass slides are immersed in dilute mixed amytriptyline and dothiepin solutions. Using Equations 4 through 8, the expected X-ray reflection curve can be calculated as a function of sulfur content. By integrating the area under the curve obtained for a fixed interval over the reflection range from when $I/I_0=0.5$ ($\theta=\theta_{0.5}$) to where $I/I_o$ is essentially 0, a relationship between curve shape and surface composition is obtained. FIG. 2 shows this calculated relationship versus surface sulfur content of the adsorbed film. From FIG. 2 it is then possible to determine directly the sulfur content of such an adsorbed film by the measurement of the integrated intensity of the X-ray reflection from the unknown film over the same range of reflection angle $\theta$. The sequence of steps involved in carrying out this calculation is illustrated in FIG. 5 of the drawings.

EXAMPLE 3

Analysis of the Oxygen Content of Silicon-Oxygen Films

Figure 3:
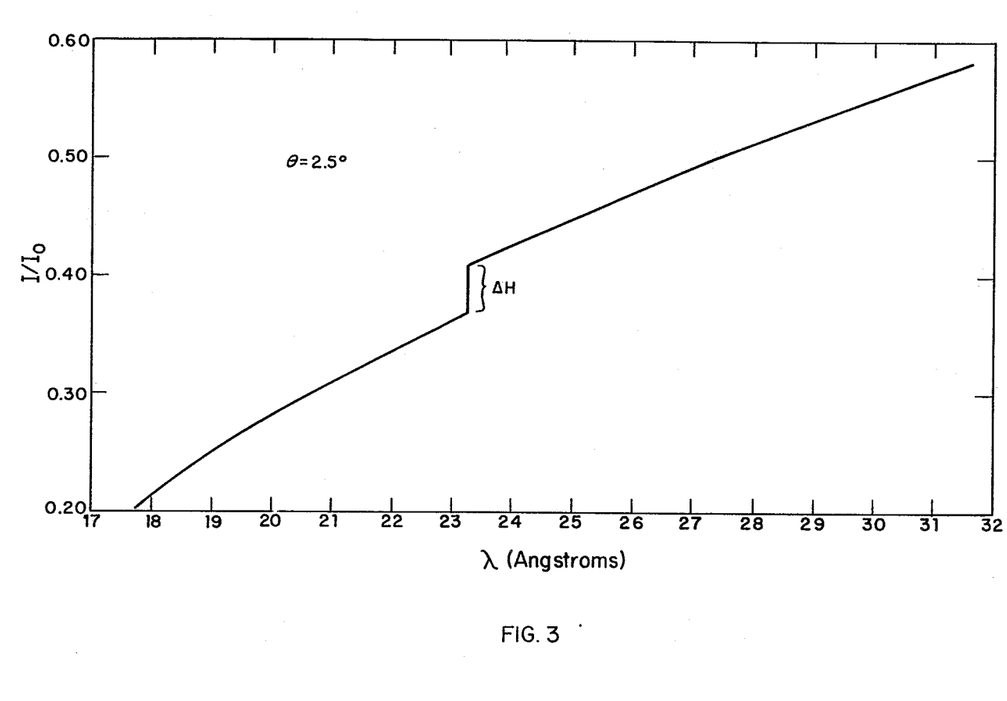
FIG. 3 depicts the calculated relationship of $I/I_o$ at a fixed value of $\theta$ for X-rays reflected from $SiO_2$ as a function of the wavelength of the incident X-rays.
Figure 4:
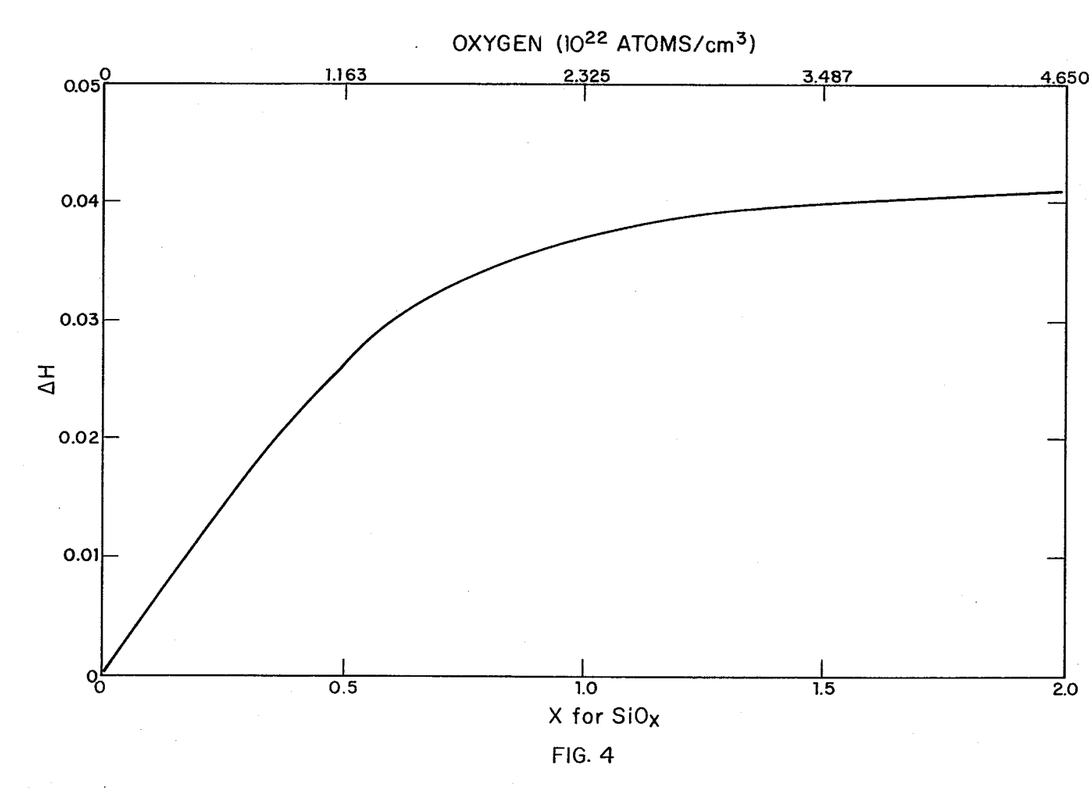
FIG. 4 depicts the relationship between the sudden drop, $\Delta H$, shown in FIG. 3 as the wavelength of the incident X-rays crosses the wavelength of the K level absorption edge of oxygen, and the oxygen content of an $SiO_x$ surface as X varies from 0 to 2.

The concentration of specific elements can be determined if a series of wavelengths are reflected from a sample and the normalized intensity of reflection at a particular fixed angle is recorded. In the case of many oxides, for example, the exact concentration of oxygen in the surface of the oxide will depend upon the time and the temperature at which the oxidation is carried out. For X-ray wavelengths in the region of the K-level absorption edge for oxygen which occurs near 23.3 angstroms, the mass absorption coefficient of oxygen for the X-rays discontinuously decreases as the X-ray wavelength increases to values larger than the K-level absorption edge. At 23.0 angstroms, for example, the mass absorption coefficient of oxygen of incident X-rays of this wavelength is very close to $21.5\times10^3$ cm$^2$/gram, while at 23.6 angstroms the mass absorption coefficient of oxygen decreases to only $1.2\times10^3$ cm$^2$/gram. Over the same wavelengthrange of 23.0 to 23.6 angstroms the mass absorption coefficient of silicon only changes from about $8.2\times10^3$ cm$^2$/gram to $8.7\times10^3$ cm$^2$/gram. Thus as the wavelength of the incident X-rays is continuously swept across the K-level absorption edge of oxygen, the reflected X-ray intensity will discontinuously change in proportion to the amount of oxygen present in the surface of the film. For the reflection of X-rays of different wavelengths from an SiO$_2$ film, FIG. 3 shows the calculated dependence of the reflected X-ray intensity at a fixed reflection angle of $\theta=2.5$ degrees as the wavelength of the incident X-rays is varied from values below the K-level absorption edge for oxygen to values above the K-level absorption edge for oxygen. The discontinuous change $\Delta H$ in normalized reflected intensity $I/I_o$ that occurs as the wavelength of the incident X-rays is increased from below 23 angstroms to above 23 angstroms can be calculated as a function of the total oxygen concentration of the surface film as calculated from the equations previously given. FIG. 4 shows this dependence. Thus, for example, if an SiO$_x$ film is found to exhibit a value of $\Delta H$ equal to 0.03, it will have an oxygen concentration of $1.395\times10^{22}$ atoms/cm$^3$. Because at the absorption edge of oxygen, the mass absorption coefficient for any other element changes only slightly as the incident wavelength is increased from just below to just above the absorption edge of oxygen, the measured discontinuous change will not vary greatly regardless of the variation in the non-oxygen concentration of the film being examined. In many microelectronic devices it is important to know the degree of oxidation of the silicon and this method as described thus provides a means for the quantitative oxygen analysis of oxidized silicon surface films.

It will be understood that various details of the invention may be changed without departing from the scope of the invention. Furthermore, the foregoing description is for the purpose of illustration only, and not for the purpose of limitation—the invention being defined by the claims.

What is claimed is:

1. An X-ray reflection method for the analysis of the relative proportions of each element in a surface composed substantially of N known elements which comprises:

subjecting said surface to X-ray radiation from at least one substantially monochromatic X-ray beam of wavelength $\lambda$ at a glancing angle $\theta$ between said beam and said surface from which the X-ray beam is reflected;

varying the glancing angle $\theta$;

measuring the reflected X-ray intensities relative to incident X-ray intensity $I_0$ of said substantially monochromatic X-ray beam as a function of the glancing angle $\theta$;

assuming any composition of said N known elements;

calculating the reflected X-ray intensities as a function of glancing angle $\theta$ and the assumed composition of said N known elements from an equation of the form $$I/I_0 = f(\theta, \lambda, \delta, \beta)$$

wherein I is the intensity of the reflected X-ray beam, $I_0$ is the intensity of the incident X-ray beam, f is the functional combination of $\theta$ the glancing angle, $\lambda$ the wavelength of the incident X-ray beam, $\delta$ the value by which the real portion of the index of refraction of the element is less than unity for incident X-rays of wavelength $\lambda$, and $\beta$ the absolute magnitude of the imaginary portion of the index of refraction of the element for incident X-rays of wavelength $\lambda$;

comparing the calculated and the measured X-ray intensities as a function of glancing angle $\theta$; and repeating the calculation of the reflected X-ray intensities as a function of glancing angle $\theta$ as a function of different assumed compositions of said N known elements until the measured X-ray intensity as a function of glancing angle $\theta$ is duplicated by the calculated X-ray intensity as a function of glancing angle $\theta$.

2. The method according to claim 1 wherein the surface to be analyzed is substantially composed of low atomic weight materials and the wavelength of the incident X-ray beam is greater than 5.4 angstroms and less than 228 angstroms.

3. The method according to claim 2 wherein the surface to be analyzed is an organic material.

4. An X-ray reflection method for the analysis of the relative proportions of each element in a surface composed substantially of N known elements which comprises:

subjecting said surface to X-ray radiation from at least one substantially monochromatic X-ray beam of wavelength $\lambda$ at a glancing angle $\theta$ between said beam and said surface from which the X-ray beam is reflected;

varying the glancing angle $\theta$;

measuring the reflected X-ray intensities relative to incident X-ray intensity $I_0$ of said substantially monochromatic X-ray beam as a function of the glancing angle $\theta$;

assuming any composition of said N known elements $\Sigma_N \rho_n$, wherein $\Sigma_N \rho_n$ represents the sum of all surface element densities $\rho_n$;

computing $\delta$, the value by which the index of refraction of the element is less than unity, for incident X-rays of wavelength $\lambda$ from an equation of the form $$\delta = \frac{e^2 \lambda^2 N_{Avo}}{2\pi mc^2} \sum_\pi \frac{\rho_n}{A_n} \left( z_n + z_{kn} \frac{\lambda^2}{\lambda_{kn}^2} \ln\left[1 - \frac{\lambda^2}{\lambda_{kn}^2}\right] \right)$$

wherein $N_{Avo}$ is Avogadro's number, $A_n$ is the molecular weight of element n, $z_n$ is the atomic number of element n, $\lambda_{kn}$ is the absorption edge of element n, $z_{kn}$ is the number electrons in the k level for element n, c is the speed of light, e is the charge of an electron, and m is the mass of an electron;

computing $\mu$, the overall linear absorption coefficient, from an equation of the form $$\mu = \sum_N (\mu_n/\rho_0)_n \rho_n$$

wherein $(\mu_n/\rho_0)_n$ is the mass absorption coefficient of element n for X-rays of wavelength $\lambda$ and $\rho_n$ is the assumed density of element n in the surface;

computing $\beta$, the absolute magnitude of the imaginary portion of the index of refraction of the element for incident X-rays of wavelength $\lambda$, from an equation of the form $$\beta = \mu\lambda/4\pi;$$

computing K from an equation of the form $$K = \beta/\delta;$$

computing $\theta_c$, the critical angle for total reflection, from an equation of the form $$\theta_c = (2\delta)^{\frac{1}{2}};$$

computing q from an equation of the form $$q = \theta/\theta_c;$$

computing $a^2/2$ from an equation of the form $$a^2/2 = q^2 - 1 + [(q^2 - 1)^2 + K^2]^{\frac{1}{2}};$$

computing a from an equation of the form $$a = \{2\{q^2 - 1 + [(q^2 - 1)^2 + K^2]^{\frac{1}{2}}\}\}^{\frac{1}{2}};$$

computing $I/I_0$, the ratio of reflected X-ray intensities to incident X-ray intensity, from an equation of the form $$\frac{I}{I_0} = \frac{1 - aq + a^2/2}{1 + aq + a^2/2};$$

comparing the calculated and the measured X-ray intensities as a function of glancing angle $\theta$; and repeating the calculation of the reflected X-ray intensities as a function of glancing angle as a function of different assumed compositions of said N known elements until the measured X-ray intensity as a function of glancing angle $\theta$ is duplicated by the calculated X-ray intensity as a function of glancing angle $\theta$.

5. The method according to claim 4 wherein the surface is composed of N known elements where N equals four or less.

6. An X-ray reflection method for determining the relative proportions of a single element in a surface composed substantially of N known elements which comprises:

subjecting said surface to X-ray radiation from at least one substantially monochromatic X-ray beam of wavelength $\lambda$ at a constant reflection angle $\theta$ between said beam and said surface from which the X-ray beam is reflected;

measuring the reflected X-ray intensity relative to incident X-ray intensity $I_0$ of said substantially monochromatic X-ray beam at said constant angle $\theta$;

repeating said measurement at said constant angle $\theta$ as said wavelength $\lambda$ is swept across the characteristic absorption wavelength of said element;

measuring the discontinuous change in reflected X-ray intensity at said constant reflection angle $\theta$ as the wavelength $\lambda$ of the incident X-rays is swept across the characteristic absorption wavelength of said element;

calculating the discontinuous change as a function of the quantity of said element in said surface; and comparing the measured discontinuous change to the calculated discontinuous change in order to determine the quantity of said element in said surface.

7. The method according to claim 6 wherein the surface is substantially composed of N known elements where N equals two.

8. An X-ray reflection method for the analysis of the relative proportions of each element in a surface composed substantially of N known elements which comprises;

subjecting said surface to X-ray radiation from at least one substantially monochromatic X-ray beam of wavelength $\lambda$ at a glancing angle $\theta$ between said beam and said surface from which the X-ray beam is reflected;

varying the glancing angle $\theta$;

measuring the reflected X-ray intensity relative to incident X-ray intensity $I_0$ of said substantially monochromatic X-ray beam as a function of the glancing angle $\theta$;

computing the integrated area under a curve representing the measured reflected X-ray intensities relative to the incident X-ray intensity $I_0$ of said substantially monochromatic X-ray beam as a function of the glancing angle $\theta$ from where $I/I_0$ is 0.5 to where $I/I_0$ is essentially zero;

assuming any composition of said N known elements $\Sigma_N \rho_n$, wherein $\Sigma_N \rho_n$ represents the sum of all surface element densities $\rho_n$;

computing $\delta$, the value by which the index of refraction of the element is less than unity, for incident X-rays of wavelength $\lambda$ from an equation of the form $$\delta = \frac{e^2\lambda^2 N_{Avo}}{2\pi mc^2} \sum_{\pi} \frac{\rho_n}{A_n} \left( z_n + z_{kn}\frac{\lambda^2}{\lambda_{kn}^2} \ln\left[1 - \frac{\lambda^2}{\lambda_{kn}^2}\right] \right)$$

wherein $N_{Avo}$ is Avogadro's number, $A_n$ is the molecular weight of element n, $z_n$ is the atomic number of element n, $\lambda_{kn}$ is the absorption edge of element n, $z_{kn}$ is the number electrons in the k level for element n, c is the speed of light, e is the charge of an electron, and m is the mass of an electron;

computing $\mu$, the overall linear absorption coefficient, from an equation of the form $$\mu = \sum_N (\mu_n/\rho_0)_n \rho_n$$

wherein $(\mu_n/\rho_0)_n$ is the mass absorption coefficient of element n for X-rays of wavelength $\lambda$, and $\rho_n$ is the assumed density of element n in the surface;

computing $\beta$, the absolute magnitude of the imaginary portion of the index of refraction of the element for incident X-rays of wavelength $\lambda$, from an equation of the form $$\beta = \mu\lambda/4\pi;$$

computing K from an equation of the form $$K = \beta/\delta;$$

computing $\theta_c$, the critical angle for total reflection, from an equation of the form $$\theta_c = (2\delta)^{\frac{1}{2}};$$

computing q from an equation of the form $$1 = \theta/\theta_c;$$

computing $a^2/2$ from an equation of the form $$a^2/2 = q^2 - 1 + [(q^2-1)^2 + K^2]^{\frac{1}{2}};$$

computing a from an equation of the form $$a = \{2\{q^2 - 1 + [(q^2-1)^2 + K^2]^{\frac{1}{2}}\}\}^{\frac{1}{2}};$$

computing $I/I_0$, the ratio of reflected X-ray intensities to incident X-ray intensity; from an equation of the form $$\frac{I}{I_0} = \frac{1 - aq + a^2/2}{1 + aq + a^2/2};$$

computing the integrated area under the curve representing the calculated reflected X-ray intensities relative to the incident X-ray intensity $I_0$ of said substantially monochromatic X-ray beam as a function of the glancing angle $\theta$ from $I/I_0$ is 0.5 to where $I/I_0$ is essentially zero as a function of said assumed composition of N known elements;

repeating the computation of the integrated area under the curve representing the calculated reflected X-ray intensities relative to the incident X-ray intensity $I_0$ of said substantially monochromatic X-ray beam as a function of the glancing angle $\theta$ from where $I/I_0$ is 0.5 to where $I/I_0$ is essentially zero as a function of different assumed compositions of N known elements; and comparing the measured integrated area to the calculated integrated areas to determine the absolute quantity of said N known elements in said surface.

9. The method according to claim 8 wherein the surface is composed substantially of N known elements where N is equal to five or less.

* * * * *